(12) United States Patent
Kolberg et al.

(10) Patent No.: US 8,761,901 B2
(45) Date of Patent: Jun. 24, 2014

(54) SYMMETRICAL CONTACT SPRING FOR SCREW HEADS

(75) Inventors: Gernot Kolberg, Berlin (DE); Carsten Schilk, Berlin (DE)

(73) Assignee: Biotronik SE & Co. KG, Berlin (DE)

(*) Notice: Subject to any disclaimer, the term of this patent is extended or adjusted under 35 U.S.C. 154(b) by 99 days.

(21) Appl. No.: 13/418,559

(22) Filed: Mar. 13, 2012

(65) Prior Publication Data
US 2012/0234660 A1    Sep. 20, 2012

(30) Foreign Application Priority Data

Mar. 17, 2011    (DE) .......................... 10 2011 001 360

(51) Int. Cl.
*A61N 1/04*    (2006.01)
(52) U.S. Cl.
USPC ......................................................... 607/119

(58) Field of Classification Search
None
See application file for complete search history.

(56) References Cited

U.S. PATENT DOCUMENTS

| | | | |
|---|---|---|---|
| 6,018,683 A | 1/2000 | Verness et al. | |
| 6,687,550 B1 | 2/2004 | Doan | |
| 2007/0055335 A1 | 3/2007 | Feldmann et al. | |
| 2007/0100209 A1* | 5/2007 | Takahashi | 600/167 |
| 2008/0103520 A1* | 5/2008 | Selkee | 606/195 |

* cited by examiner

*Primary Examiner* — Brian T Gedeon
*Assistant Examiner* — Ankit Tejani
(74) *Attorney, Agent, or Firm* — Buchanan Ingersoll & Rooney PC

(57) ABSTRACT

A contact spring for the electrical contact of an electrode housing, which is located at the distal end of an electrode line, and a shaft located inside the electrode housing, the contact spring having an external diameter having a center point, which is connectable to the housing in an electrically conductive manner.

16 Claims, 1 Drawing Sheet

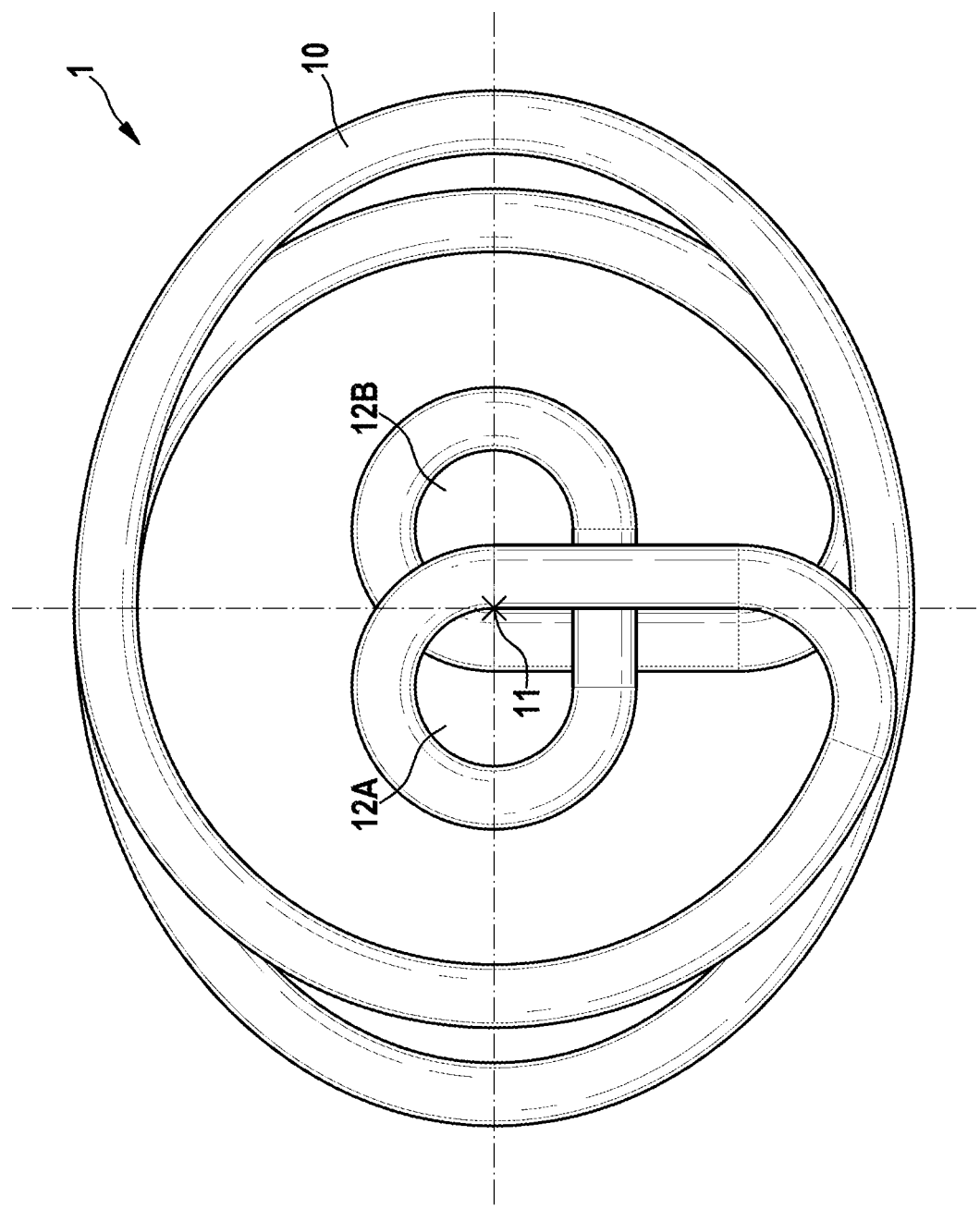

SYMMETRICAL CONTACT SPRING FOR SCREW HEADS

CROSS-REFERENCE TO RELATED APPLICATIONS

This patent application claims the priority of co-pending German Patent Application No. DE 10 2011 001 360.1, filed on Mar. 17, 2011 in German Patent Office, the disclosure of which is hereby incorporated by reference in its entirety.

TECHNICAL FIELD

The present disclosure is directed towards an electrode line for implantation in a living body and a contact spring for the electrical contact between an external housing, for example, an electrode head housing, and an internal coil, which is used for the active fastening of the electrode line, for example.

An electrode line of the type mentioned at the beginning generally comprises an elongated electrode body, typically made of an electrically insulating material, a rotatable electrical supply line, which extends in the electrode body, and an electrode head at the distal end of the electrode body. The electrode head generally comprises, inter alia, a housing, an electrically conductive shaft, which is mounted so that it is rotatable and axially displaceable therein with the aid of the supply line, and which is attached to the supply line in axial extension, a corkscrew like screw-in electrode on the shaft, and a contact spring, which is inserted between the housing and the shaft for their electrical connection.

BACKGROUND

Various contact springs are already established in the market. According to one embodiment, it is a coiled compression spring. It builds up the contact force in the axial direction between a contact bearing on the fixation axis and a counter bearing in the housing. This design has the particular disadvantage that the spring covers the entire threaded area of the fixation, i.e., typically approximately 2 mm. The spring produces an electrical contact in all positions. The length of the compressed spring must also be added to the length of the head. If the head additionally receives a seal, the length thereof must also be added thereto. An electrode head having this type of spring is therefore too long for many applications.

In another version, the contact force is built up radially between the shaft and the housing, which is known from U.S. Publication No. 2007/0055335, for example. A coiled spring for the electrical connection between the electrode housing and the shaft is disclosed therein, which is implemented as an essentially level coiled spring revolving around the shaft under spring tension, and which has sliding contact with the housing and/or the shaft at its leg ends while exerting a radially oriented spring force. A contact spring of this construction has the problem that the radial contact force acts on one side on the shaft of the fixation. The shaft requires a radial counter bearing on which friction can occur. This friction increases the number of turns to unscrew the fixation from the electrode head.

The present inventive disclosure is directed toward overcoming one or more of the above-identified problems.

An object is therefore to avoid the problems of the cited prior art and to provide a contact spring which has the smallest possible axial extension, and in which one sided radial forces do not occur or are at least compensated for, as well as an electrode line, which has the smallest possible electrode head and the longest possible flexible section.

An object is achieved by features of the independent claim (s). Favorable embodiments and advantages of the present invention will be apparent from the further claims and the description.

SUMMARY

A contact spring, which has an outer contour and a central axis, for the electrical contact of an external housing, for example, an electrode head housing having a shaft mounted inside the housing, is distinguished in that the wire of the contact spring is shaped so that it forms at least two legs inside the outer contour, the location of the at least two legs in the contacted state of the contact spring being moved away from a predetermined location in the non-contacted state due to force action originating from the housing or from the shaft.

The two legs are used for the purpose of accommodating or mounting a shaft so that it can slide and is axially displaceable. In the contacted state, a location change results in relation to the predetermined location of the legs with respect to the outer contour of the contact spring in the non-contacted state. The tension conditions inside the contact spring change in relation to the non-contacted state, the tension conditions arising through forces induced by displacing the legs from their predetermined location or by compression of the outer contour, for example. This change of the tension conditions causes an electrical contact between each leg and the shaft, on the one hand, and between the outer contour and the housing, on the other hand.

In a first embodiment, each of the two legs is located laterally offset to the central axis of the contact spring in the non-contacted state. In the contacted state of the contact spring, the legs are located, displaced from their prior location, substantially aligned with the central axis. This location is achieved in that the legs are displaced from their predetermined location by force action on the legs. For example, it arises in that the legs are aligned by a shaft extending through the central axis of the contact spring. They preferably have the same distance to the central axis, and are also preferably diametrically opposite with respect to the central axis. Forces of equal absolute value arise during the above mentioned pre-tensioning due to the symmetry thus existing, the forces mutually canceling out on the shaft because of the diametrical alignment of the center point axes of the legs. A one sided load is therefore avoided, which remedies the mentioned disadvantages of the prior art. In addition, the reliability of the contact between the shaft having the electrical fixation, which is similar to a coiled compression spring, and the electrode head housing is improved, since the contact is provided redundantly.

If the two legs are preferably eyes, they have a center point. The center points of these two eyes are each on a center point axis, these axes extending parallel to the central axis of the contact spring. The outer contour of the contact spring approximately corresponds to the inner contour of the hollow cylindrical electrode head housing. If the two laterally offset, preferably diametrically offset eyes are centered by a deflection movement (caused by threading in the shaft), the outer contour of the contact spring widens in diameter so that the diameter is greater than the inner contour of the electrode head housing. However, the outer diameter cannot widen due to the spatial delimitation because of the inflexible inner contour of the housing, whereby pre-tensioning occurs on the eyes, which is reflected in an electrical contact of the eyes with the shaft and the housing.

It is also conceivable in an alternative second embodiment that the contact spring is manufactured so that the legs are not offset laterally to the central axis in the non-contacted state, i.e., they are located aligned in the central axis of the contact spring. The shaft is also mounted so it can slide and is axially displaceable in the legs in this embodiment. However, in this case, the contacted state is achieved by a change of the diameter of the outer contour, in that it is reduced by force action pointing in the direction of the central axis. The outer contour is thus compressed in the contacted state in relation to the non-contacted state. For this purpose, it is necessary for the diameter of the outer contour to be greater in the relaxed, non-contacted state than the inner contour of the external housing, which is to be contacted with the shaft. Upon insertion of the contact spring into the housing, this outer contour is pressed radially inward and inserted into the housing. The contacted state results because the legs are moved away from the original position, which is aligned with the central axis, in that they are pushed radially outward. An electrical contact to the shaft thus results. The legs can also be designed in this embodiment as eyes.

In both embodiments, the contact spring is preferably constructed as a leg spring—i.e., a coiled spring which is loaded by torsion around its axis—which forms the outer contour of the contact spring with its outer diameter. Since the axial extension of the electrode head is primarily dependent on the contact spring, the axial extension of the latter must be kept small, typically, for example, at a level of 0.1 mm to 5 mm, and preferably 0.5 mm, to obtain the smallest possible electrode head. In order to increase the reliability, this coiled spring generally consists of four to ten wire windings, preferably four to six, and particularly preferably four wire windings, which extend around the central axis of the contact spring. A wire winding in the meaning of the patent application is the extension of the wire having a wraparound angle of 360°, the pitch corresponding to the single wire diameter. A sufficient contact between the contact spring and the electrode head housing is ensured by the four windings. Furthermore, the outer contour preferably has a cross-section which is polygonal, and preferably triangular, or rounded, or from the circular, oval, or curved of constant width.

In both embodiments of the contact springs, preferably at most two of the four wire windings of the contact springs are shaped or bent radially inward from the external diameter and form the mentioned legs, with these at most two windings being smaller in their diameter than the external diameter. The diameters of these two windings are preferably dimensioned so that the shaft is mounted so that it is rotationally and axially displaceable inside the electrode housing of the mentioned type. These are preferably the two middle windings. It is thus ensured that the force engagement points in the case of tensioning are axially close to one another because the eyes are located directly adjacent to one another, so that it is ensured that the two diametrically extending force vectors substantially compensate for one another. In the embodiment(s) mentioned herein, the electrical contact to the housing is also ensured by the two windings, which are still located in the external diameter of the leg spring and, therefore, on the outer contour of the contact spring.

In addition, the contact spring can be produced from any type of wire. Preferably, the wire is a round or flat wire. However, other types of wire can be used. In particular, MP35N or medical stainless steel such as, for example, chromium cobalt alloys suggests itself as the material, or also titanium, tantalum, platinum, or alloys of multiple or all of these three elements. Coated wires, so called "plated wires", are also conceivable.

The electrode line for cardiological use, which has already been mentioned several times in the preceding embodiments, comprises:
    an elongated electrode body made of an electrically insulating material,
    a rotatably mounted electrical supply line, which extends in the electrode body, and
    an electrode head at the distal end of the electrode body having
        a hollow-cylindrical electrode head housing,
        an electrically conductive shaft, which is mounted so that it is rotatable and axially displaceable in the electrode head housing with the aid of the supply line, and which is fastened on the supply line in axial extension,
        a rigid screw-in electrode, which is like a coiled compression spring, on the shaft, and
        a contact spring, which is inserted between the housing and the shaft, according to the above-described object of the patent application for the purpose of the electrical connection between the housing and the shaft, the contact spring having an external diameter which can be contacted in an electrically conductive manner with the housing.

The electrode line is distinguished in that the shaft is mounted so that it can slide and is axially displaceable between the two legs of the contact spring, and spring forces oriented radially outward act on the legs due to the contact spring, which is brought into electrical contact, so that the location of the legs is thus moved away from the predetermined location in the non-contacted state and an electrical contact thus results between the housing and the shaft. In the installed state, the inner structure, or the form of the contact spring, is thus changed so that tension thus arises, which results in an above described displacement of the legs with respect to their original location in the non-contacted state. The forces acting radially outward are preferably essentially identical in absolute value, but act in diametrically opposite directions. The shaft is thus freed from single sided loading.

To ensure the essentially equal force application, the housing has a shaft bearing which mounts the shaft on a housing central axis, whereby the spring forces oriented radially outward mutually compensate for one another.

The electrode line is a so-called actively fixable electrode line. This means that the electrode can be fastened in the tissue by means of the (corkscrew like) screw-in electrode, which is like a coiled compression spring. In order to perform the screwing in movement, the physician can rotate the electrical supply line, which can also be extendable in the axial direction, around its axis during the implantation, and thus set the screw-in electrode into rotation. For this purpose, the electrode line comprises a rotatable plug or rotatable plug pin on the diametrically opposite proximal end.

FIG. 1 shows a contact spring 1 according to the first embodiment of an object of this patent application. The contact spring 1 of this exemplary embodiment is shaped from a leg spring 10 shaped from a wire, which has an external diameter having a central axis 11. The external diameter is designed so that it can be inserted and electrically connected in a housing of an electrode head (not shown here). The contact spring 1 is inserted into the hollow cylindrical housing of the electrode head so that the central axis is located on the longitudinal extension axis of the hollow cylindrical housing. The wire is formed so that two eyes 12A and 12B, which each have a center point, result inside the external diameter. The center points of the eyes 12A, 12B are each located on an axis which extends parallel to the central axis 11. The eyes 12A, 12B are used to accommodate a shaft (also not shown here), which is mounted in the electrode housing, the shaft bearing being positioned so that the shaft is typically located close to or on the longitudinal extension axis of the hollow cylindrical electrode head and, therefore, also on the central axis 11 of the contact spring. The center points of the eyes 12A and 12B are not located on the central axis 11 of the contact spring in the rest state, but rather are offset laterally on both sides of the central axis 11. The distance between each of the center point axes of the eyes 12A, 12B and the central axis 11 is preferably equal. The contact spring is only pre-tensioned by threading the shaft into the eyes 12A, 12B, i.e., the center point axes of the eyes 12A and 12B are displaced by the shaft of the electrode line onto the central axis 11 of the contact spring and held thereon.

In the exemplary embodiment shown, the leg spring consists of four windings, the two outer windings having the complete wraparound angle forming the external diameter of the leg spring and, therefore, the outer contour of the contact spring 1, while the two inner windings are shaped or bent radially inward from the external diameter and form the eyes 12A and 12B. Only the two inner windings are only subject to a pre-tension when the shaft is threaded into the shaft and a deformation also only then results therein, while the two outer windings are pressed against the inner contour of the electrode head housing because of the deformation of the inner windings. The deformation arises due to the above-described forces acting radially diametrically outward. These forces ensure that the eyes 12A, 12B are continuously in electrical contact with the shaft, which is mounted so it can slide and rotate in these eyes 12A, 12B.

The contact spring 1 is laid in the housing in the relaxed rest state. The eyes 12A, 12B are subsequently moved so that their center point axes are located on the central axis 11 of the contact spring 1. The shaft is subsequently guided along the center point axes 11 through the two eyes 12A, 12B and thus into the shaft bearing, so that it is located along the longitudinal extension axis of the housing. When the shaft pulls the eyes 12A, 12B into the contact spring central axis 11, the respective radii of the contact springs opposite to the eyes 12A, 12B build up a force against the housing. The forces engaging on the shaft are symmetrical and compensate for one another. The shaft is mounted by the spring so that it can slide and is axially displaceable. A contact force simultaneously arises between the housing wall and the contact spring 1. The electrical contact is reliably secured. The contact is also maintained upon deflection of the shaft, because the contact always tightens on one side. The screwing in and out behavior is thus significantly improved in threaded electrodes.

It will be apparent to those skilled in the art that numerous modifications and variations of the described examples and embodiments are possible in light of the above teachings of the disclosure. The disclosed examples and embodiments are presented for purposes of illustration only. Other alternate embodiments may include some or all of the features disclosed herein. Therefore, it is the intent to cover all such modifications and alternate embodiments as may come within the true scope of this invention, which is to be given the full breadth thereof. Additionally, the disclosure of a range of values is a disclosure of every numerical value within that range.

We claim:

1. A contact spring for electrical contact of an electrode head housing with a shaft mounted inside the electrode head housing, the contact spring having an outer contour having a central axis, the outer contour being able to be contacted in an electrically conductive manner with the electrode head housing, wherein wire of the contact spring is shaped so that it forms at least two legs inside the outer contour, a location of the at least two legs in a contacted state of the contact spring being moved away by force action from a predetermined location in a non-contacted state, wherein the at least two legs are located laterally offset to the central axis of the contact spring in the non-contacted state, and are located aligned with the central axis, displaced by force action on the at least two legs from their predetermined locations, in the contacted state.

2. The contact spring according to claim 1, wherein the outer contour is formed from four to ten wire windings.

3. The contact spring according to claim 2, wherein the wire windings are wound around the central axis so that the outer contour has a cross-section which is polygonal, triangular, rounded, circular, oval, or curved of constant width.

4. The contact spring according to claim 2, wherein at most two of the wire windings are shaped or bent radially inward by an external diameter, the at most two of the windings being smaller in their diameter than the external diameter.

5. The contact spring according to claim 4, wherein the at most two of the wire windings which are shaped or bent radially inward form the at least two legs.

6. The contact spring according to claim 5, wherein the at least two legs each form an eye.

7. The contact spring according to claim 1, wherein the at least two legs each have a same distance to the central axis of the contact spring.

8. The contact spring according to claim 1, wherein each of the at least two legs is located diametrically opposite with respect to the central axis of the contact spring.

9. A contact spring for electrical contact of an electrode head housing with a shaft mounted inside the electrode head housing, the contact spring having an outer contour having a central axis, the outer contour being able to be contacted in an electrically conductive manner with the electrode head housing, wherein wire of the contact spring is shaped so that it forms at least two legs inside the outer contour, a location of the at least two legs in a contacted state of the contact spring being moved away by force action from a predetermined location in a non-contacted state, wherein the at least two legs are located aligned with the central axis in the non-contacted state, and the contacted state is achieved by force action, which points in a direction of the central axis, on the outer contour, whereby the at least two legs are moved away from the predetermined location.

10. The contact spring according to claim 1, wherein the contact spring has a height of 0.5 mm to 5 mm.

11. The contact spring according to claim 1, wherein the wire is a round or flat wire.

12. The contact spring according to claim 1, wherein the contact spring is constructed as a leg spring.

13. A contact spring for electrical contact of an electrode head housing with a shaft mounted inside the electrode head housing, the contact spring having an outer contour having a central axis, the outer contour being able to be contacted in an electrically conductive manner with the electrode head housing, wherein wire of the contact spring is shaped or bent radially inward so that it forms at least two legs inside the outer contour, wherein the at least two legs each form an eye having a center point, wherein the center points of the at least two eyes are located diametrically opposite to the central axis of the contact spring in the non-contacted state, and are located aligned with the central axis, displaced by force action on at least one of the at least two legs and the outer contour from their predetermined locations, in the contacted state.

14. The contact spring according to claim 13, wherein the outer contour is formed from four to ten wire windings.

15. The contact spring according to claim 14, wherein the wire windings are wound around the central axis so that the outer contour has a cross-section which is polygonal, triangular, rounded, circular, oval, or curved of constant width.

16. The contact spring according to claim 13, wherein the contact spring has a height of 0.5 mm to 5 mm.

* * * * *